(12) United States Patent
Heidrich et al.

(10) Patent No.: US 9,097,648 B2
(45) Date of Patent: Aug. 4, 2015

(54) METHOD OF DETECTING MOLECULES AND OPTICAL SENSOR

(75) Inventors: Helmut Heidrich, Berlin (DE); Peter Lützow, Berlin (DE); Daniel Pergande, Berlin (DE); Wolfgang Schade, Goslar (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 25 days.

(21) Appl. No.: 14/112,976

(22) PCT Filed: Apr. 19, 2012

(86) PCT No.: PCT/EP2012/001175
§ 371 (c)(1),
(2), (4) Date: Jan. 7, 2014

(87) PCT Pub. No.: WO2012/143072
PCT Pub. Date: Oct. 26, 2012

(65) Prior Publication Data
US 2014/0118741 A1    May 1, 2014

(30) Foreign Application Priority Data
Apr. 21, 2011  (EP) ..................................... 11075072

(51) Int. Cl.
| G01N 21/00 | (2006.01) |
| G01N 21/25 | (2006.01) |
| G01N 21/77 | (2006.01) |
| G01N 21/27 | (2006.01) |
| G01N 21/39 | (2006.01) |
| G01N 21/17 | (2006.01) |

(52) U.S. Cl.
CPC .............. *G01N 21/255* (2013.01); *G01N 21/27* (2013.01); *G01N 21/7746* (2013.01); *G01N 21/39* (2013.01); *G01N 2021/1731* (2013.01); *G01N 2021/7789* (2013.01)

(58) Field of Classification Search
None
See application file for complete search history.

(56) References Cited

FOREIGN PATENT DOCUMENTS

| EP | 1804052 A1 | 7/2007 |
| EP | 2053385 A2 | 4/2009 |

(Continued)

OTHER PUBLICATIONS

Armani, Andrea M. et al., "Heavy Water Detection Using Ultra-High-Q Microcavities", Optics Letters, vol. 31, No. 12, Jun. 15, 2006, pp. 1896-1898.

(Continued)

*Primary Examiner* — Tri T Ton
(74) *Attorney, Agent, or Firm* — Faegre Baker Daniels LLP

(57) ABSTRACT

The present disclosure relates to an example method and optical sensor for detecting molecules of a particular substance by means of an optical sensor. Such an example method may include bringing the sensor into contact with a fluid to be analyzed, coupling light of a first wavelength into an optical resonator of the optical sensor, coupling light of a second wavelength into the same resonator or into a second optical resonator of the optical sensor, detecting, for each of the first and the second wavelengths, an optical signal coupled out of an optical path containing the respective resonator, varying an optical length of the respective resonator or the respective wavelength and detecting a broadening of this resonance indicating an absorption of the light fed into the respective resonator by molecules accumulated at the active layer of this resonator.

13 Claims, 3 Drawing Sheets

(56) References Cited

FOREIGN PATENT DOCUMENTS

| GB | 2222881 A | 3/1990 |
|---|---|---|
| WO | 2012143072 A1 | 10/2012 |

OTHER PUBLICATIONS

Boyd, Robert W. et al., "Sensitive disk resonator photonic biosensor", Applied Optics, vol. 40, No. 31, Nov. 1, 2001, pp. 5742-5747.

Farca, G. et al., "Cavity-enhanced laser absorption spectroscopy using microresonator whispering-gallery modes", OPTICS EXPRESS, vol. 15, No. 25, Jan. 1, 2007, p. 17443-17448.

'Gaussian Function', Wikipedia, Apr. 1, 2011, pp. 1-7, XP055008115, Retrieved from the Internet: URL http://en.wikipedia.org/windex.php?title=special: book&bookcmd=download&collection_id=711b65882614538e&writer=rl&retrun_to=GaussianFunctions, section Properties.

Hu, Juejun et al., "Cavity-Enhanced IR Absorption in Planar Chalcogenide Glass Microdisk Resonators: Experiment and Analysis", Journal of Lightwave Technology, vol. 27, No. 23, Dec. 1, 2009, pp. 5240-5245.

International Preliminary Report on Patentability issued in PCT/EP2012/001175, completed Jul. 15, 2013, 22 pages.

International Search Report and Written Opinion issued in PCT/EP2012/001175, mailed Jul. 24, 2012, 18 pages.

Jokerst, Nan et al., "Chip Scale Integrated Microresonator Sensing Systems", Journal of Biophotonics, vol. 2, No. 4, pp. 212-226.

Lutzow, Peter et al., "Integrated Optical Sensor Platform for Multiparameter Bio-Chemical Analysis", Optics Express, vol. 19, No. 14, Jul. 4, 2011, pp. 13277-13284.

Nitkowski, Arthur et al., "Cavity-enhanced on-chip absorption spectroscopy using microring resonators", OPTICS EXPRESS, vol. 16, No. 16, Aug. 4, 2008, pp. 11930-11936.

Nitkowski, Arthur et al., "On-Chip Spectrophotometry for Bioanalysis Using Nanophotonic Devices", 2010 Conference on Lasers and Electro-Optics (CLEO), 16, May 2010, pp. 1-2.

Sun, Yuze et al., "Optical ring resonators for biochemical and chemical sensing", Analytical and Bioanalytical Chemistry, vol. 399, 2011, pp. 205-211.

Yariv, A. "Universal relations for coupling of optical power between microresonators and dielectric waveguides", Electronics Letters, vol. 36, No. 4, Feb. 17, 2000, pp. 321-322.

|   | Substance 1 | Substance 2 | Substance 3 |
|---|---|---|---|
| $\lambda_1$ | x | x |   |
| $\lambda_2$ | x |   | x |
Fig. 5
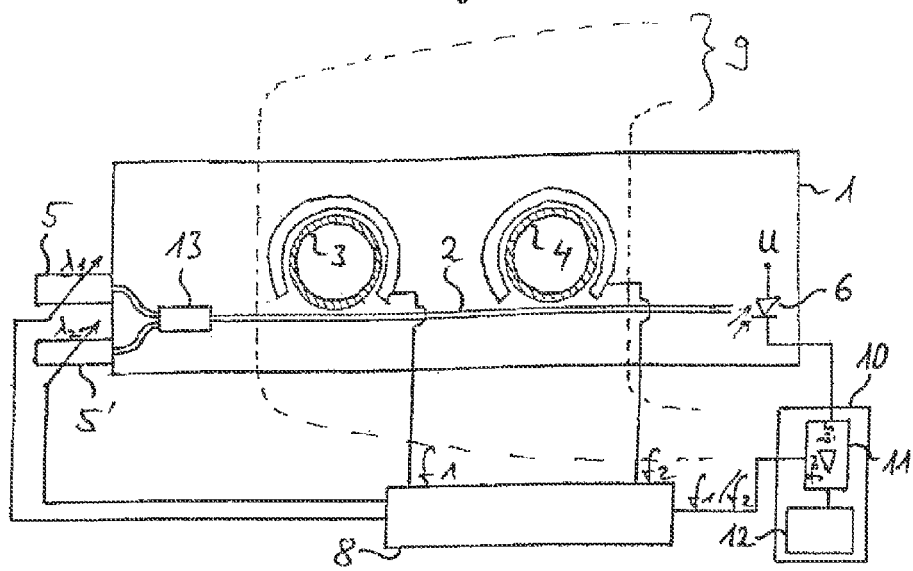
Fig. 6
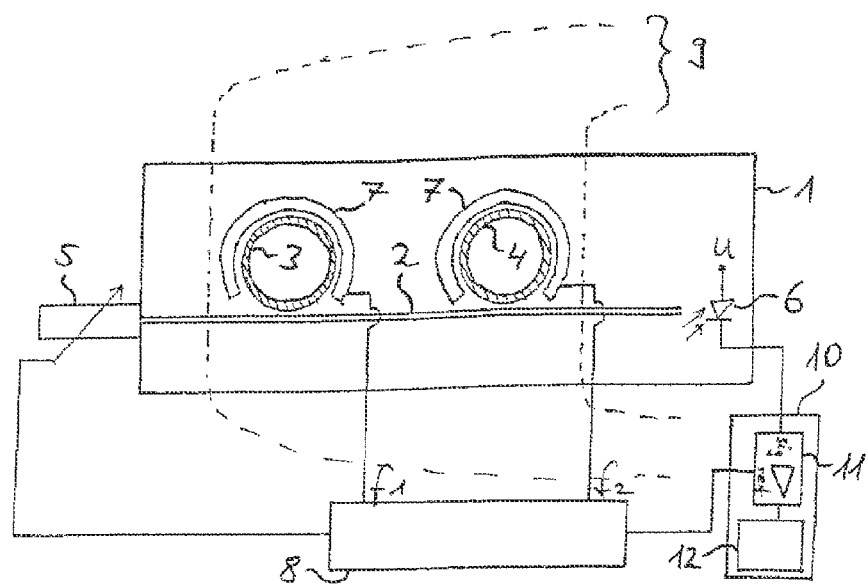
Fig. 7

METHOD OF DETECTING MOLECULES AND OPTICAL SENSOR

CROSS-REFERENCE TO RELATED APPLICATIONS

This application is a national phase application of PCT Application No. PCT/EP2012/001175, internationally filed Apr. 19, 2012, which claims priority to European Application No. 11 075 072.6, filed Apr. 21, 2011, both of which are herein incorporated by reference in their entirety.

TECHNICAL FIELD

The present disclosure relates to a method for detecting molecules of a particular substance as well as to an optical sensor designed for performing this method.

BACKGROUND

The document EP 2 270 478 A1 describes an optical sensor comprising an optical path, a light source for generating light and for feeding this light into the optical path, and a photo detector for detecting an optical signal coupled out of the first optical path. In addition, the optical path comprises, among other components, an optical resonator covered at least partially with an active layer of a covering material for selectively adsorbing molecules of a particular kind. A measurement implemented with this sensor makes use of the influence of adsorbed molecules on the optical length of the resonator, which causes resonance frequencies associated with a corresponding resonator to shift. In turn, this shift can be detected by observing the light emitted from the optical path. Thus, it is possible to detect whether a fluid which is brought into contact with the active layer contains molecules of the particular kind.

Even if very selective materials are used for the active layer, this layer will adsorb not only molecules of exactly one substance but rather molecules of a whole group of substances. This applies in particular for substances which are chemically similar. For this reason, ambiguities currently remain in the art as to whether the detected molecules are truly of a particular substance to be detected or only chemically similar to the particular substance.

SUMMARY

It is an objective of the present invention to suggest a more precise method and a corresponding sensor for detecting molecules of a particular substance while avoiding the ambiguities of prior molecule detection methods. Furthermore, the methods and apparatuses disclosed herein perform the corresponding measurements quickly while expending limited resources.

The present disclosure presents an example method for detecting molecules of a particular substance via an optical sensor. Such an example method may include bringing the sensor into contact with a fluid to be analyzed. Furthermore, the example method may include coupling light of a first wavelength into an optical resonator of the sensor. In an aspect, the resonator may be covered at least partially with an active layer of a covering material for selectively adsorbing a group of substances comprising the substance to be detected. The example method may further include coupling light of a second wavelength into the same resonator or into a second optical resonator of the sensor, the second resonator being covered at least partially with an active layer of the same covering material. Moreover, the example method may include detecting, for each of the first and the second wavelengths, an optical signal coupled out of an optical path containing the respective resonator. Such a method may additionally include varying, for each of the first and the second wavelengths, an optical length of the respective resonator or the respective wavelength such that an interval comprising at least one resonance of the respective resonator is scanned. Additionally, such a method may include detecting, for each of the first and the second wavelengths, a broadening of the resonance indicating an absorption of the light fed into the respective resonator by molecules accumulated at the active layer of the resonator. Furthermore, the method may include detecting the broadening of a resonance means, in some contexts, detecting or measuring a width of the corresponding resonance and comparing this width with a reference value. The reference value may be chosen to be the width of the same resonance in a situation when the sensor is not in contact with (and, thus, not influenced by) the fluid to be analyzed. It may, for example, be defined as the width of the respective resonance measured when the sensor is brought into contact with a reference fluid like, for example, water or with air. The broadening of the different resonances may be detected in that the same measurements are additionally preformed before bringing the sensor into contact with the fluid to be analyzed or once more after removing the fluid to be analyzed from the sensor and/or after bringing the sensor into contact with the reference fluid.

Any usual measure may be used for defining the width of the respective resonance. The width may, for example, be defined as a full width at half maximum of or as a difference between two wavelengths separated by a resonance wavelength of the respective resonance and corresponding to inflection points or points of maximum slope of two edges of this resonance.

In this context, the term fluid may denote any analyte. In particular, this term may denote a liquid or a gas.

By the presently described methods, information is obtained not only as to whether molecules of any substance contained in the fluid have been adsorbed by the active layer or layers. Instead, information about a light absorbing behaviour of these molecules is also obtained for two different wavelengths where the first wavelength and the second wavelength are different. This helps to determine which substance of a potential group of substances for which the active layer acts as a selective adsorber. Of course the method can be generalized by performing the same analysis for at least one further wavelength.

Furthermore, it is possible, after performing the steps described above, to decide whether the fluid contains molecules of the substance to be detected depending on whether a broadening of the resonance—or a broadening exceeding a certain threshold—can be detected only for the first wavelength or only for the second wavelength or for both wavelengths. The method may, thus, further include identifying whether the fluid contains molecules of the substance to be detected in a significant concentration depending on whether a broadening exceeding a certain threshold is detected only for the first wavelength or only for the second wavelength or for both wavelengths. To this end, the first and the second wavelength can be selected to be typical absorption wavelengths of one or more but not all of the substances of the group of substances.

A difference between the first and the second wavelength may be chosen at least one order of magnitude larger, and sometimes several orders of magnitude larger, than a spacing between adjacent resonances of the resonator or of each of the resonators at the respective wavelength. In this context, an order of magnitude may be understood as a factor of ten.

In an example embodiment of the method, a shift of the resonance can be determined for at least one of the first and the second wavelengths. In addition to the broadening, the shift can indicate a change of the optical length of the respective resonator caused by the molecules accumulated at the active layer of this resonator. This makes the analysis more precise as the shift indicates that molecules have been adsorbed by the active layer and can even be taken as a measure of an amount of the adsorbed substance so that the broadening can be evaluated taking into account the amount of the absorbed substance. In particular, the aforementioned thresholds for the broadening of the resonances applied for deciding whether one or another of the substances is contained in the fluid can be defined depending on the shift of one or the other of the resonances.

The broadening of the resonance can be easily detected by determining, within said interval, a derivative of the optical signal with respect to the wavelength and by determining a spacing between two extremes of the derivative at the resonance. This spacing may be a measure of the broadening. More precisely, the two extremes can be two maxima of an absolute value of the derivative. To this end, the derivative can be determined by means of a lock-in amplifier by modulating the optical length of the resonator or the wavelength with a modulation signal, feeding an output of a photo detector used for detecting the optical signal into the lock-in amplifier, and using the modulation signal as a reference signal for the lock-in amplifier.

In order to detect molecules of a particular substance as described here above, two similar optical sensors may be used, with both realising the same idea as discussed above.

In a first example embodiment of the present disclosure, the optical sensor for detecting molecules of a particular substance may include a first optical path, a first light source for generating light of a first wavelength, and a first photo detector. The first light source may be optically coupled to the first optical path for feeding the light of the first wavelength into the first optical path. Additionally, the first photo detector may be optically coupled to the first optical path for detecting an optical signal coupled out of the first optical path.

Furthermore, the sensor may further include a second optical path, a second light source for generating light of a second wavelength, and a second photo detector. The second light source may be optically coupled to the second optical path for feeding the light of the second wavelength into the second optical path. Moreover, the second photo detector may be optically coupled to the second optical path for detecting an optical signal coupled out of the second optical path.

Each of the first and the second optical paths may comprise an optical resonator covered at least partially with an active layer of a covering material for selectively adsorbing a group of substances comprising the substance to be detected. Additionally, the covering material may be the same for the resonator of the first optical path and the resonator of the second optical path. The resonators of both optical paths and/or the first and the second light sources may be tunable for varying an optical length of the resonators and/or the first and the second wavelengths.

In addition, the sensor may further comprise a control unit for controlling the light sources and/or the resonators. This control unit may be configured to vary the optical lengths of the resonators and/or the first and the second wavelengths such that an interval comprising at least one resonance of the respective resonator is scanned.

In some examples, the first and the second wavelengths may be different. For example, a difference between the first wavelength and the second wavelength may be at least one order of magnitude, and sometimes several orders of magnitude, larger than a spacing between adjacent resonances of each of the resonators at the respective wavelength. In each case, the interval scanned by varying the first and the second wavelengths or equivalently the wavelength interval scanned by shifting said resonance by varying the optical length of the respective resonator may be at least one order of magnitude smaller than the difference between the first and the second wavelength. This also applies to the second embodiment described below. Thus, even if the first and the second wavelengths are varied, they can be clearly distinguished from each other as to different wavelengths or wavelength intervals.

In a second embodiment of the invention, the optical sensor for detecting molecules of a particular substance may include an optical path, at least one light source for generating light of a first wavelength and of a second wavelength, and a photo detector. In an aspect, the at least one light source may be optically coupled to the optical path for coupling the light of the first wavelength and of the second wavelength into the same optical path.

Furthermore, the photo detector may be optically coupled to the optical path for detecting an optical signal coupled out of the optical path. In this case, the optical path may include an optical resonator covered at least partially with an active layer of a covering material for selectively adsorbing a group of substances comprising the substance to be detected. Again, a difference between the first and the second wavelengths may be at least one order of magnitude or even several orders of magnitude larger than a spacing between adjacent resonances of the resonator at each of the first and the second wavelengths. In an example aspect, the resonator and/or the at least one light source are tunable for varying an optical length of the resonator and/or the first and the second wavelengths, the sensor including a control unit.

The control unit may be configured for controlling the at least one light source such that the light of the first wavelength and the light of the second wavelength are successively fed into the optical path. The control unit may be further configured for varying the optical length of the resonator and/or the first and the second wavelengths such that, for each of the first and the second wavelengths, an interval comprising at least one resonance of the resonator is scanned. Furthermore, the control unit may be configured for detecting, for each of the first and the second wavelengths, a width and/or a broadening of this resonance.

In both embodiments, the sensor can advantageously be used for performing the detecting method described above. At the same time it has a rather simple structure and can be realized in a compact and robust form.

To this end, the sensor or components thereof, such as the optical path or the optical paths including the resonator or resonators, can be realized on a chip as a so-called integrated optical circuit. The optical path or each of the first and the second optical paths may comprise one or two optical waveguides for coupling the resonators of the optical path or of the first and the second optical paths to the respective light source and to the respective photo detector in order to make sure that the sensor is compact and robust. The waveguides can be designed as photonic wires.

Each of the resonators can preferably be realized as a ring resonator, such as a so called micro-ring resonator. The ring resonators can be coupled to the respective waveguide or waveguides by evanescent fields. They are particularly well suited as they show a very high sensitivity for molecules accumulated at a surface. This means that their optical length depends very sensitively on an amount of molecules adsorbed by the active layer. However, other types of optical resonators may be used instead of ring resonators, for example Fabry-Pérot resonators.

The sensor may, in addition, have a channel for conducting the fluid to be analyzed to the active layer of the resonator of each optical path. The at least one light source or the first and the second light sources may be chosen as lasers which are appropriate for their monochromatic light.

The sensor may comprise a signal processing unit for analyzing an output of the first and the second photo detectors, or, in the second embodiment, the output of a single photo detector. This signal processing unit include the control unit. The signal processing unit can be configured for determining, within the scanned intervals, a derivative of the optical signal with respect to the wavelength. To this end, the control unit can be configured for modulating, for each of the first and the second optical paths or for the only optical path, the optical length of the respective resonator or the respective wavelength with a modulation signal. In this case, the signal processing unit may comprise, for determining said derivative, a lock-in amplifier, the control unit being connected to the lock-in amplifier for feeding the modulation signal as a reference signal into the lock-in amplifier. The derivative may be obtained as an output of the lock-in amplifier. It is equivalent, of course, whether the light source or the optical length of the resonator is modulated and whether the light source or the resonator is varied in order to scan the interval around the first and the second wavelengths. An example solution may be obtained by tuning the light source for scanning said interval and to modulate the respective resonator (e.g., electro-optically or thermo-optically) for determining the derivative.

Determining the derivative of the respective optical signal with respect to the wavelength is desirable for easier determining a measure of the width and, thus, of the broadening of the respective resonance.

In preferred embodiments the signal processing unit of the sensor is configured for determining, for each of the two wavelengths or for each of the resonators, a measure of a width and/or of a broadening of the resonance of the respective resonator comprised by the scanned interval. If the derivative is determined as described above, the signal processing unit can be configured for doing so by determining a spacing between two extremes of the derivative at the resonance, the spacing being the measure of the width and/or the broadening in this case.

In order to get more information about the substances contained in the fluid to be detected and in order to achieve more precise results, the signal processing unit can be further configured for determining, for at least one of the resonators, a shift of the resonance comprised by the scanned interval.

It is possible that the optical path or each of the optical paths comprises at least one further optical resonator covered at least partially with an active layer of a further covering material for selectively adsorbing molecules, the further covering material being different from the aforementioned covering material or containing the same substance but in a different concentration. Depending on how the selectively adsorbing covering materials are chosen, this enables the sensor to be used for simultaneously detecting a presence or absence of molecules of different substances and/or for an even more precise detection of molecules of the particular substance sought. In this case it is essential that the resonators (i.e., their optical length) can be modulated in order to identify the resonances that can be attributed to a particular resonator.

In the embodiment with the first and the second optical paths, the sensor may optionally comprise at least one further optical path, a further light source for generating light of a further wavelength, and a further photo detector. In some examples, the further light source may be optically coupled to the further optical path for feeding the light of the further wavelength into the further optical path, and the further photo detector may be optically coupled to the further optical path for detecting an optical signal coupled out of the further optical path. In this case, the at least one further optical path may also include an optical resonator covered at least partially with an active layer of the same covering material as used for the resonators of the first and the second optical paths. Additionally, the resonator of the further optical path and/or the further light source may be tunable for varying an optical length of this resonator and/or the further wavelength. In some examples, the control unit may also be configured for varying the optical length of this resonator and/or the further wavelength such that an interval comprising at least one resonance of the resonator of the further optical path is scanned. Hereby, ambiguities, which are caused by the fact that the active layers are not selective enough, can be further reduced.

The covering materials used for the active layers of the sensors described here may be, for example, molecular imprinted polymers. The ambiguities which are reduced by the suggested method and sensors are due to the fact that not only molecules of one particular substance, but also similar substances that may have certain structures in common with the substance to be detected and may be therefore adsorbed by these active layers.

A resonance of the respective optical resonator is broader at a wavelength at which the molecules accumulated at the resonator show a higher absorption rate. Thus, additional information about the absorbing behaviour of the adsorbed molecules for at least two different wavelengths is obtained by the method and the sensors described herein. This information helps to reduce the aforementioned ambiguities as some of the substances of the group of substances which may be adsorbed by the active layer can be excluded if this substance has a high absorption rate at the first or the second wavelength and if no broadening of a resonance can be seen at this particular wavelength.

BRIEF DESCRIPTION OF THE DRAWINGS

Exemplary embodiments of the invention are explained hereafter with reference to FIGS. 1 to 7.

FIG. 5 is a table illustrating different possible results obtained in a measurement performed with the sensor of FIG. 1, FIG. 6 is a schematic top view of an optical sensor in a second embodiment, and FIG. 7 is a schematic top view of an optical sensor in a further embodiment only slightly different to the embodiment of FIG. 6.

DETAILED DESCRIPTION

Figure 1:
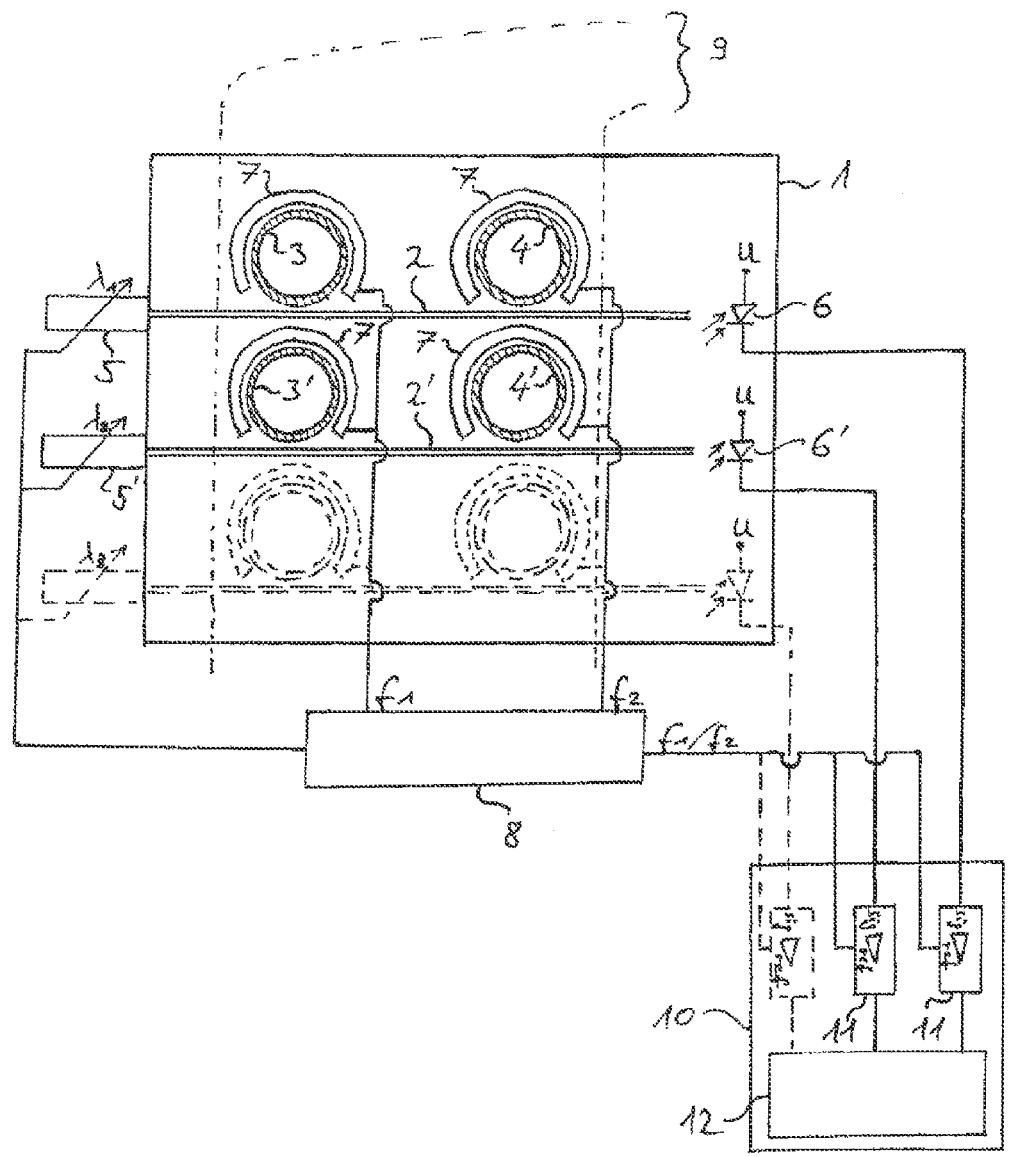
FIG. 1 is a schematic top view of an optical sensor in a first embodiment, this sensor comprising two or more optical paths with several ring resonators.

FIG. 1 shows an optical sensor for analyzing fluids and for detecting molecules of one or several particular substances in a fluid to be analyzed. Components of this sensor are realized in planar technology on a chip 1 and form an integrated optical circuit. This integrated optical circuit has a first optical path comprising an optical waveguide 2, an optical ring resonator 3 and a further optical ring resonator 4 as well as a second optical path comprising a waveguide 2', an optical ring resonator 3' and a further optical ring resonator 4'. All these ring resonators 3, 3', 4, and 4' are micro rings of a diameter of between 10 µm and 200 µm and are realized, as the waveguides 2, and 2', as photonic wires. They are coupled to waveguide 2 or 2' of the respective optical path via evanescent fields.

A first light source 5 is optically coupled to the waveguide 2 for feeding light of a first wavelength $\lambda_1$ into the first optical path. Likewise, a second light source 5' is coupled to the waveguide 2' for feeding light of a second wavelength $\lambda_2$ into the second optical path. Both light sources 5 and 5' are tunable lasers so that the two wavelengths $\lambda_1$ and $\lambda_2$ can be varied to a certain extent.

At an opposite end of the two optical paths, the waveguide 2 is optically coupled to a first photo detector 6 for detecting an optical signal coupled out of the first optical path while the waveguide 2' is optically coupled to a second photo detector 6 for detecting an optical signal coupled out of the second optical path. In this example case, the photo detectors 6 and 6' are realized as phododiodes on the chip 1.

Each of the resonators 3 and 3' is covered with an active layer of a covering material for selectively adsorbing molecules of a group of substances comprising a particular substance to be detected. The covering material is the same for the resonators 3 and 3' and may be, e.g., a Molecularly Imprinted Polymer (MIP). Similarly, the further resonators 4 and 4' are covered with an active layer of another covering material for selectively adsorbing molecules of another group of substances comprising the same or another substance to be detected, this covering material being the same for the further resonators 4 and 4' but different from the covering material of the resonators 3 and 3'. The active layers are visualized by shadings. An optical length of each of the resonators 3, 3', 4, and 4' can be modulated electro-optically or thermo-optically by means of electrodes 7.

As indicated in FIG. 1 by dashed lines, the sensor may comprise a further optical path of the same structure as the first and the second optical paths, a further light source for generating light of a further wavelength $\lambda_3$, for feeding the light of the further wavelength $\lambda_3$ into the further optical path and a further photo detector for detecting an optical signal coupled out of the further optical path. In this case, the further optical path comprises an optical resonator and a further optical resonator as well, each of the optical resonators being covered with an active layer of the same covering material as used for the resonators 3, 3' or the further resonators 4, 4' of the first or the second optical path, respectively. Furthermore, the further light source is tunable as the first and the second light sources 5 and 5', and the resonator and the further resonator of the further optical path can be modulated together with the resonators 3 and 3' and the further resonators 4 and 4' of the first and the second optical paths.

The sensor comprises a control unit 8 for controlling the light sources 5 and 5' and the resonators 3 and 3' as well as the further resonators 4 and 4'. The control unit 8 is configured for varying the optical lengths of the resonators 3 and 3' by a modulation signal of a frequency $f_1$ and to correspondingly modulate the further resonators 4 and 4' by a modulation signal of a different frequency $f_2$. Where applicable, the same applies for the resonator and the further resonator of the further optical path. Furthermore, the control unit 8 is configured for varying the first wavelength $\lambda_1$ and the second wavelength $\lambda_2$ such that an interval comprising at least one resonance of the respective resonator 3 or 3' and of the respective further resonator 4 or 4' is scanned. Where applicable, the control unit 8 is similarly configured for additionally varying the further wavelength $\lambda_3$ such that at least one resonance of each of the resonator and the further resonator of the further optical path are scanned.

It should be noted that each of the optical paths might have a different waveguide for optically coupling the resonators 3 or 3' and 4 or 4' to the respective photo detector 6 or 6' respectively. In this case, the waveguides 2 and 2' may be used for coupling them to the respective light source 5 or 5' respectively.

On top of the chip 1, a microfluidic channel 9 is provided for conducting the fluid to be analyzed to the active layers of the different resonators 3, 3', 4, and 4'.

For analyzing an output of the first photo detector 6 and the second photo detector 6' and where applicable of the further photo detector, the sensor comprises a signal processing unit 10 with lock-in amplifiers 11 and an evaluation unit 12. The signal processing unit 10 is configured for determining, for each of the resonators 3, 3', 4, and 4', a measure of a broadening of the resonance of the respective resonator 3, 3', 3 or 4' comprised by the respective wavelength interval which is scanned by tuning the light sources 5 and 5'. To this end, the signal processing unit 10 is configured for determining, within each of the scanned intervals, a derivative of the respective optical signal with respect to the wavelength. This is done by means of the respective lock-in amplifier 11, the control unit 8 being connected to the lock-in amplifier 11 for feeding one of the modulation signals as a reference signal into the lock-in amplifier. The modulation signal of the frequency $f_1$ is used as reference signal if the resonances of the resonators 3 and 3' are to be investigated, while the frequency $f_2$ is chosen for the reference signal for investigating the resonances of the further resonators 4 and 4'. Depending on whether the reference signal is chosen to have the frequency $f_1$ or $f_2$, the respective lock-in amplifier 11 filters a contribution of the resonator 3 or 3' or of the further resonator 4 or 4' out of the respective optical signal. An output of the respective lock-in amplifier 11 corresponds to the derivative of this contribution to the optical signal with respect to the wavelength.

At each resonance of the respective resonator 3, 3', 4' or 4', an absolute value of this derivative shows two maxima. The evaluation unit 12 is configured for determining a spacing between these two maxima, this spacing being a measure of a broadening of this resonance. In addition, the evaluation unit 12 is configured for determining, for each of the resonators 3, 3', 4, and 4', a shift of the resonance comprised by the scanned interval.

Hereafter, an analysis of the fluid conducted by the channel 9 using the resonators 3 and 3' is described. In the same way, the further resonators 4 and 4' can be used for an additional analysis of this fluid in order to get additional or more precise information about what kind of substances are contained in the fluid.

Figure 2:
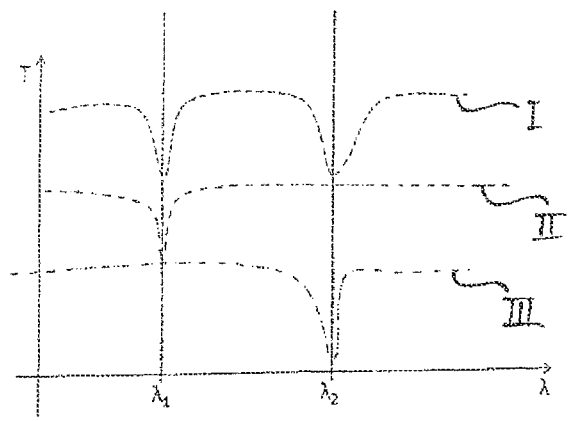
FIG. 2 is a diagram showing, in a schematic way, typical transmission spectra of three different substances.
Figure 3:
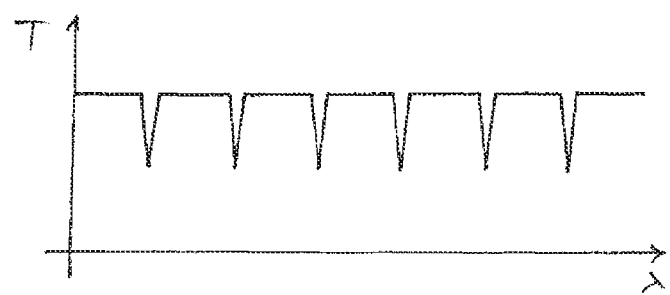
FIG. 3 is a diagram showing, in a schematic way, a transmission spectrum of an optical path comprising a ring resonator as contained in the optical sensor of FIG. 1.

FIG. 2 shows, as an example, a transmission spectrum I of a first substance, a transmission spectrum II of a second substance II and a transmission spectrum III of a third substance. It is assumed that these three substances form the aforementioned group of substances preferentially adsorbed by the active layers of the resonators 3 and 3'. Reflecting a typical situation, the first substance shows a high absorption at the two wavelengths $\lambda_1$ and $\lambda_2$ while the second substance shows a high absorption only at the first wavelength $\lambda_1$ and the third substance only at the second wavelength $\lambda_2$. An example difference between these two wavelengths $\lambda_1$ and $\lambda_2$ may be something like 300 nm while a spacing between adjacent resonances of the ring resonators 3, 3', 4, and 4' may be about two orders of magnitude smaller and has a value of about 2 nm. FIG. 3 shows a transmission spectrum of one of the optical paths. Some of the resonances of the respective resonator 3 or 3' (a contribution of the corresponding further resonator 4 or 4' being neglected for simplicity) can clearly be seen in this diagram. The light sources 5 and 5' are chosen and tuned to produce light of the absorption wavelength $\lambda_1$ or $\lambda_2$, respectively, and to vary the respective wavelength slightly so that a small interval comprising one of the resonances of the respective resonator 3 or 3' is scanned.

Figure 4:
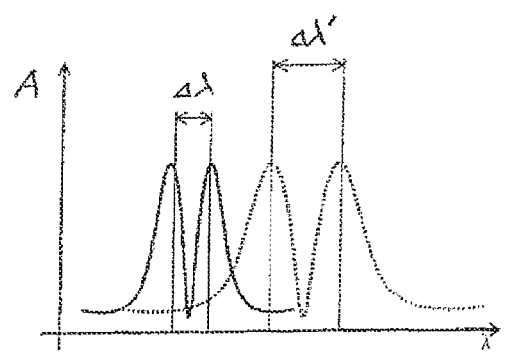
FIG. 4 is a diagram showing, in a schematic way, an output of one of several lock-in amplifiers contained in a signal processing unit of the sensor of FIG. 1, this output being plotted for two different cases as a function of a wavelength in a neighbourhood of a resonance of one of the ring resonators.

FIG. 4 shows an output of the lock-in amplifier 11 within the scanned wavelength interval. It is assumed that the reference signal is chosen to have the frequency $f_1$ used for modulating the resonators 3 and 3' in this case. As explained above, the output of the amplifier 11 corresponds to a wavelength derivative of a contribution of the resonator 3 or 3' respectively to the optical signal coupled out of the respective optical path. A solid line shows the output in a situation when no molecules absorbing light of the respective wavelength $\lambda_1$ or $\lambda_2$ are accumulated at the active layer of the respective ring resonator. A dotted line shows a corresponding signal after accumulating molecules at the active layer which do absorb light of the respective wavelength $\lambda_1$ or $\lambda_2$. The accumulation of light absorbing molecules results in, both, a shift and a broadening of the resonance, the enlarged spacing $\Delta\lambda'$ between the two maxima of the output shown in FIG. 4 (compared to the spacing AA before the accumulation of absorbing molecules) being a measure of this broadening. The evaluation unit 12 is configured to detect the shift indicating that a certain amount of molecules have been adsorbed by the active layer and the enlarged spacing $\Delta\lambda'$ indicating to what degree these molecules have an absorbing behaviour for light of the respective wavelength $\lambda_1$ or $\lambda_2$.

By conducting the fluid to be analyzed through the channel 9, this fluid is brought into contact with the resonators 3, 3', 4, and 4' and in particular with the active layers thereon. If the fluid contains any of the three substances mentioned above, molecules of the respective substance will be adsorbed by and accumulated on the active layers of the resonators 3 and 3'. A measurement of the shift of the resonances caused by this accumulation alone indicates that any of the substances of said group of substances is contained in the fluid. It does not yet, however, answer the question as to whether the substance contained in the fluid is, for example, the first, the second or the third substance of the group. This question, however, may be answered using the result of the detection of the broadening of the resonances. This is illustrated in the table of FIG. 5. This table shows for the three substances mentioned above in the context of FIG. 2 and for the two wavelengths $\lambda_1$ and $\lambda_2$ whether a resonance at the respective wavelength $\lambda_1$ or $\lambda_2$ will be broadened or not if the resonators 3 and 3' have been in contact with the respective substance, an X indicating a broadening in each case. If a broadening can be seen only for $\lambda_1$, it can be concluded that the fluid contains the second substance. If a broadening can be seen only for $\lambda_2$, the fluid contains the third substance. If a broadening is detected for both wavelengths $\lambda_1$ and $\lambda_2$, the fluid contains the first substance or, both, the second and the third substance.

In order to detect the broadening of the different resonances, the same measurements are preformed not only after bringing the fluid into contact with the resonators 3, 3', 4, and 4', but also before bringing the sensor into contact with this fluid or once more after removing the fluid to be analyzed from the sensor or after bringing the sensor into contact with a reference fluid, such as, for example, clean water or air. The respective broadening may then be defined as $\Delta\lambda'-\Delta\lambda$, wherein $\Delta\lambda$ is the width of the respective resonance measured when the sensor is not in contact with the fluid to be analysed and $\Delta\lambda'$ is the width of the same resonance measured after bringing the sensor into contact with this fluid.

The evaluation unit 12 is configured to perform this analysis by a method for pattern recognition after determining the shifts and broadenings of the resonances contained in the scanned intervals.

FIGS. 6 and 7 show two similar optical sensors. The features explained above in the context the sensor shown in FIG. 1 are marked with the same reference signs. The only difference between the sensor of FIG. 6 and the sensor of FIG. 1 is that the sensor of FIG. 6 has only one optical path. By means of a coupler 13, light of both wavelengths $\lambda_1$ and $\lambda_2$ generated by the two light sources 5 and 5' can be fed into the waveguide 2 of this optical path. The control unit 8 is, in this embodiment, configured for controlling the two light sources 5 and 5' such that the light of the first wavelength $\lambda_1$ and the light of the second wavelength $\lambda_2$ are successively fed into the waveguide 2 via the coupler 13. hus, the method for analyzing the fluid described above can be performed analogously with this sensor.

The sensor of the embodiment shown in FIG. 7 differs from the example shown in FIG. 6 in that this sensor has a single light source 5 which is, in this case, tunable over a range which is large enough to cover both wavelengths $\lambda_1$ and $\lambda_2$ so that no second light source is needed to perform the method described above. The signal processing unit 10 may of course, in the embodiment of FIG. 7 as well as in the embodiments of FIG. 1 and FIG. 6, be comprised by or being understood as part of the control unit 8.

The invention claimed is:

1. A method for detecting molecules of a substance, comprising:
    bringing an optical sensor into contact with a fluid to be analysed;
    coupling light of a first wavelength into an optical resonator of the optical sensor, the optical resonator being covered at least partially with an active layer of a covering material for selectively adsorbing a group of substances comprising the substance;
    coupling light of a second wavelength into one of optical resonator and a second optical resonator of the optical sensor, the second optical resonator being covered at least partially with an active layer of the covering material, wherein a difference between the first wavelength and the second wavelength is at least one order of magnitude larger than a spacing between adjacent resonances of the resonator or of the resonators at the respective wavelength;

detecting, for each of the first and the second wavelengths, an optical signal coupled out of an optical path containing a respective resonator of the optical resonator and the second optical resonator;

varying, for each of the first and the second wavelengths, at least one of an optical length of the respective resonator and the respective wavelength such that an interval comprising at least one resonance of the respective resonator is scanned; and detecting, for each of the first and the second wavelengths, a broadening of the resonance indicating an absorption of the light fed into the respective resonator by molecules accumulated at the active layer of the respective resonator; and identifying whether the fluid contains molecules of the substance to be detected in a significant concentration depending on whether a broadening exceeding a certain threshold is detected only for the first wavelength or only for the second wavelength or for both wavelengths.

2. The method of claim 1, wherein the broadening of the resonance is detected by determining, within the interval, a derivative of the optical signal with respect to the wavelength and by determining a spacing between two extremes of the derivative at the resonance, the spacing being a measure of the broadening.

3. The method of claim 2, wherein the derivative is determined by a lock-in amplifier by:
modulating at least one of the optical length of the resonator and the wavelength with a modulation signal;
feeding an output of a photo detector used for detecting the optical signal into the lock-in amplifier; and
using the modulation signal as a reference signal for the lock-in amplifier.

4. The method of claim 1, wherein, for at least one of the first and the second wavelengths, a shift of the resonance is determined in addition to the broadening, the shift of the resonance indicating a change of the optical length of the respective resonator caused by the molecules accumulated at the active layer of the respective resonator.

5. An optical sensor for detecting molecules of a substance, comprising:
a first optical path, a first light source for generating light of a first wavelength, and a first photo detector, the first light source being optically coupled to the first optical path for feeding the light of the first wavelength into the first optical path, the first photo detector being optically coupled to the first optical path for detecting an optical signal coupled out of the first optical path;
the optical sensor further comprising a second optical path, a second light source for generating light of a second wavelength, and a second photo detector, the second light source being optically coupled to the second optical path for feeding the light of the second
second photo detector being optically coupled to the second optical path for detecting an optical signal coupled out of the second optical path;
wherein each of the first and the second optical paths comprises an optical resonator covered at least partially with an active layer of a covering material for selectively adsorbing a group of substances comprising the substance to be detected, the covering material being the same for the resonator of the first optical path and the resonator of the second optical path;
wherein a difference between the first wavelength and the second wavelength is at least one order of magnitude larger than a spacing between adjacent resonances of each of the resonators at the respective wavelength; and wherein the resonators of at least one of both optical paths and the first and the second light sources are tunable for varying at least one of an optical length of the resonators and the first and the second wavelengths;
the optical sensor further comprising a control unit for controlling at least one of the light sources and the resonators, and a signal processing unit for analyzing an output of the first and the second photo detectors, the control unit being configured for varying at least one of the optical lengths of the resonators and the first and the second wavelengths such that an interval comprising at least one resonance of the respective resonator is scanned, the signal processing unit being configured for determining, for each of the resonators, a measure at least one of a width and a broadening of the resonance of the respective resonator comprised by the interval.

6. The optical sensor of claim 5, wherein each of the first and the second optical paths comprises one or two optical waveguides for coupling the resonators of the first and the second optical paths to the respective light source and to the respective photo detector.

7. The optical sensor of claim 5, wherein the resonators are ring resonators.

8. The optical sensor of claim 5, wherein the signal processing unit is configured for determining, within the interval, a derivative of the optical signal with respect to the wavelength and by determining a spacing between two extremes of the derivative at the resonance, the spacing being the measure of the width or the broadening.

9. The optical sensor of claim 8, wherein the control unit is configured for modulating, for each of the first and the second optical paths, at least one of the optical length of the respective resonator or the respective wavelength with a modulation signal, and wherein the signal processing unit for determining the derivative comprises a lock-in amplifier, the control unit being connected to the lock-in amplifier for feeding the modulation signal as a reference signal into the lock-in amplifier.

10. The optical sensor of claim 5, wherein the signal processing unit is further configured for determining, for at least one of the resonators, a shift of the resonance comprised by the interval.

11. The optical sensor of claim 5, further comprising at least one further optical path, a further light source for generating light of a further wavelength, and a further photo detector, the further light source being optically coupled to the further optical path for feeding the light of the further wavelength into the further optical path, the further photo detector being optically coupled to the further optical path for detecting an optical signal coupled out of the further optical path;
wherein the at least one further optical path comprises an optical resonator covered at least partially with an active layer of the same covering material;
wherein at least one of the resonator of the further optical path and the further light source are tunable for varying an optical length of this resonator or the further wavelength; and
wherein the control unit is further configured for varying at least one of the optical length of this resonator and the further wavelength such that an interval comprising at least one resonance of the resonator of the further optical path is scanned.

12. The optical sensor claim 5, wherein each of the optical paths comprises at least one further optical resonator covered at least partially with an active layer of a further covering material for selectively adsorbing molecules, the further covering material being different from the aforementioned covering material or having a different concentration.

13. An optical sensor for detecting molecules of a particular substance, comprising:

an optical path, at least one light source for generating light of a first wavelength and of a second wavelength, and a photo detector, the at least one light source being optically coupled to the optical path for coupling the light of the first wavelength and of the second wavelength into the same optical path, the photo detector being optically coupled to the optical path for detecting an optical signal coupled out of the optical path;

wherein the optical path comprises an optical resonator covered at least partially with an active layer of a covering material for selectively adsorbing a group of substances comprising the substance to be detected;

wherein a difference between the first wavelength and the second wavelength is at least one order of magnitude larger than a spacing between adjacent resonances of each of the resonators at the respective wavelength; and wherein at least one of the resonator and the at least one light source are tunable for varying at least one of an optical length of the resonator and the first and the second wavelengths;

the optical sensor further comprising a control unit, the control unit being configured:

for controlling the at least one light source such that the light of the first wavelength and the light of the second wavelength are successively fed into the optical path;

for varying at least one of the optical length of the resonator and the first and the second wavelengths such that, for each of the first and the second wavelengths, an interval comprising at least on resonance of the resonator is scanned; and for detecting, for each of the first and the second wavelengths, at least one of a width and a broadening of the resonance.

* * * * *